US006780639B1

(12) United States Patent
Chtarto et al.

(10) Patent No.: US 6,780,639 B1
(45) Date of Patent: Aug. 24, 2004

(54) ANTIBIOTIC INDUCIBLE/REPRESSIBLE GENETIC CONSTRUCT FOR GENE THERAPY OR GENE IMMUNIZATION

(75) Inventors: Abdelwahed Chtarto, Brussels (BE); Liliane Tenenbaum, Ittre (BE); Marc Levivier, Waterloo (BE); Marc Peschanski, Créteil (FR); Jacques Brotchi, Brussels (BE); Thierry Velu, Brussels (BE)

(73) Assignee: Universite Libre de Bruxelles (BE)

( * ) Notice: Subject to any disclaimer, the term of this patent is extended or adjusted under 35 U.S.C. 154(b) by 0 days.

(21) Appl. No.: 09/645,162

(22) Filed: Aug. 24, 2000

Related U.S. Application Data (60) Provisional application No. 60/150,484, filed on Aug. 24, 1999.

(51) Int. Cl.[7] .......................... C12N 15/74; C12N 5/02; A61K 48/00; A61K 31/70

(52) U.S. Cl. .................. 435/320.1; 435/325; 435/455; 424/93.21; 514/44

(58) Field of Search ............................ 435/320.1, 325; 435/455; 514/44; 424/93.21

(56) References Cited

U.S. PATENT DOCUMENTS

| 5,891,718 A | 4/1999 | Hobart et al. | |
|---|---|---|---|
| 6,004,941 A | * 12/1999 | Bujard et al. ................. | 514/44 |

FOREIGN PATENT DOCUMENTS

| WO | WO 9429442 | 12/1994 |
|---|---|---|
| WO | WO 95/28493 | 4/1995 |
| WO | WO 96/33731 | * 10/1996 |
| WO | WO 97/35992 | 3/1997 |
| WO | WO 99/09054 | 2/1999 |

OTHER PUBLICATIONS

P Wu et al., Journal of Virology, "Adeno–Associated Virus Vector–Mediated Transgene Integration into Neurons and Other Nondividing Cell Targets," Jul. 1998, vol. 72, No. 7, pp. 5919–5926.*

RP Haberman et al., Gene Therapy, "Inducible long–term gene expression in brain with adeno–associated virus gene transfer" 1998,5,pp. 1604–1611.*

S Irniger et al., Molecular and Cellular Biology, "Different Classes of Polyadenylation Sites in the Yeast Saccharomyces cerevisiae," Jun. 1991, vol. 11, No. 6, pp. 3060–3069.*

A Hofmann et al., Proc.Natl.Acad. Sci. USA, "Rapid retroviral delivery of tetracycline–inducible genes in a single autoregulatory cassette," May 1996, vol. 93, pp. 5185–5190.*

M Gossen et al., Science, "Transcriptional Activation by Tetracyclines in Mammalian Cells," Jun. 1995, vol. 268, pp. 1766–1769.*

PE Shockett et al., Proc.Natl.Acad.Sci. USA, "Diverse strategies for tetracycline–regulated inducible gene expression," May 1996, vol. 93, pp. 5173–5176.*

SA–Mohammadi et al., Gene Therapy, "Efficient transgene regulation from a single tetracylcine–controlled positive feedback regulatory system," 1998, 5, pp. 76–84.*

(List continued on next page.)

*Primary Examiner*—Anne M. Wehbe
*Assistant Examiner*—Janice Li
(74) *Attorney, Agent, or Firm*—Knobbe, Martens, Olson & Bear, L L P (57) ABSTRACT

The present invention is related to an antibiotic inducible/repressible genetic construct for controlling the transcription of a gene of interes: by a cell. The genetic construct comprises a bi-directional antibiotic controlled activator-responsive promoter/operator sequence which is located between the gene of interest and a cistron encoding a reverse antibiotic controlled transactivator and controls the transcription of the gene of interest and of the cistron.

13 Claims, 4 Drawing Sheets

OTHER PUBLICATIONS

RC Boucher, Journal of Clinical Investigation, "Status of gene therapy for cystic fibrosis lung disease," Feb. 1999, vol. 103, No. 4, pp. 441–445.*

SL Eck et al., Pharmacological Basis of Therapeutics, "Gene–Based Therapy," 1995, Chap.5, 9th Ed., pp. 77–101.

Antibiotics PubMed May 10, 2002.*

Appendix A; Vector Information, Tet Systems User Manual, pp. 37, 39 ,6.

A. Freese et al., Direct gene transfer into human epileptogenic hippocampal tissue with an adeno–associated virus vector: implications for a gene therapy approach to epilepsy, Epilepsia, vol. 38, No. 7, Jul. 1997, pp. 759–766.

Terence R. Flotte et al., Expression of the Cystic Fibrosis Transmembrane Conductance Regulator from a Novel Adeno–associated Virus Promoter, The Journal of Biological Chemistry, vol. 268, No. 5, Feb. 15, 1993, pp. 3781–3790.

M.J. During et al., In vivo expression of therapeutic human genes for dopamine production in the caudates of MPTP–treated monkeys using an AAV vector, Gene Therapy, vol. 5, 1998, pp. 820–827.

Ronald L. Klein et al., Neuron–Specific Transduction in the Rat Septohippocampal or Nigrostriatal Pathway by Recombinant Adeno–associated Virus Vectors, Experimental Neurology, vol. 150, 1998, pp. 183–194.

Udo Baron et al., Co–regulation of two gene activities by tetracycline via a bidirectional promoter, Nucleic Acids Research, vol. 23, No. 17, 1995 pp. 3605–3606.

Deniz Kirik et al., Long–Term rAAV–Mediated Gene Transfer of GDNF in the Rat Parkinson's Model: Intrastriatal But Not Intranigral Transduction Promotes Functional Regeneration in the Lesioned Nigrostriatal System, The Journal of Neuroscience, vol. 20, No. 12, Jun. 15, 2000, pp. 4686–4700.

T. Tenenbaum et al., Cellular contaminants of adeno–associated virus vector stocks can enhance transduction, Gene Therapy, vol. 6, 1999, pp. 1045–1053.

Zolotukhin et al., Recombinant adeno–associated virus purification using novel methods improves infectious titer and yield, Gene Therapy, vol. 6, 1999, pp. 973–985.

P. Wu et al., An AAV promoter–driven neuropeptide Y gene delivery system using Sendai virosomes for neurons and rat brain, Gene Therapy, vol. 3, 1996, pp. 246–253.

Richard J. Samulski et al., Cloning of adeno–associated virus into pBR322: Rescue of intact virus from the recombinant plasmid in human cells, Proc. Natl. Acad. Sci. USA, vol. 79, Mar. 1982, p. 2077–2081.

Susan K. McLaughlin et al., Adeno–Associated Virus General Transduction Vectors: Analysis of Proviral Structures, Journal of Virology, vol. 62, No. 6, 1988, pp. 1963–1973.

Richard Jude Samulski et al., Helper–Free Stocks of Recombinant Adeno–Associated Viruses: Normal Integration Does Not Require Viral Gene Expression, Journal of Virology, vol. 63, No. 9, Sep. 1989, pp. 3822–2828.

Thomas J. McCown et al., Differential and persistent expression patterns of CNS gene transfer by an adeno–associated virus (AAV) vector, Brain Research, vol. 713, 1996, pp. 99–107.

Delphine Bohl et al., Control of Erythropoietin Delivery by Doxycycline in Mice After Intramuscular Injection of Adeno–Associated Vector, Blood, vol. 92, No. 5, Sep. 1, 1998, pp. 1512–1517.

R.P. Haberman et al., Inducible long–term gene expression in brain with adeno–associated virus gene transfer, Gene Therapy, vol. 5, 1998, pp. 1604–1611.

Werner Paulus et al., Self–Contained, Tetracycline–Regulated Retroviral Vector System for Gene Delivery to Mammalian Cells, Journal of Virology, vol. 70, No. 1, Jan. 1996, pp. 62–67.

Ralph Witzgall et al., The Krüppel–associated box–A (KRAB–A) domain of zince finger proteins mediates transcriptional repression, Proc. Natl. Acad. Sci. USA, vol. 91, May 1994, pp. 4514–4518.

S.B. Dunnett et al., Staging and dissection of rat embryos, Neural Transplantation A Practical Approach, pp. 1–201.

Ping Wu et al., Adeno–Associated Virus Vector–Mediated Transgene Integration into Neurons and Other Nondividing Cell Targets, Journal of Virology, vol. 72, No. 7, Jul. 1998, pp. 5919–5926.

Manfred Gossen et al., Transcriptional Activation by Tetracyclines in Mammalian Cells, Science, vol. 268, Jun. 23, 1995, pp. 1766–1769.

A–Mohammadi, et al., "Efficient transgene regulation from a single tetracycline–controlled positive feedback regulatory system," Gene Therapy, 5:1, pp. 76–84, 1998.

Klein, et al., "Recombinant adeno–associated virus (AAV) vectors for brain–derived neurotrophic factor (BDNF) and growth–associated protein (GAP–43) gene delivery," Soc. Neurosci.Abstr., vol. 22, Part 1, p. 316, 1996.

Rosenblad, et al., "Glial cell line–derived neurotrophic factor increases survival, growth and function of intrastriatal fetal nigral dopaminergic grafts," Neuroscience, 75:4, pp. 979–985, 1996.

Tenenbaum, et al., "AVV–mediated transduction of human fetal brain tissue," Soc. Neurosci. Abstr., vol. 25, Part 1, p. 212, 1999.

Patent European Search Report from Priority Application EP 00 87 0183 dated Jan. 17, 2001.

Du, et al. 1996. Efficient transduction of human neurons with an adeno–associated virus vector Gene Therapy, 3:254–261.

During, et al. 1998. In vivo expression of therapeutic human genes for dopamine production in the caudates of MPTP–treated monkeys using an AAV vector. Gene Therapy, 5:820–827.

Fan, et al. 1998. Prevention of dopaminergic neuron death by adeno–associated virus vector–mediated GDNF gene transfer in rat mesencephalic cells in vitro. Neuroscience Letters, 248:61–64.

Kaplitt, et al. 1994. Long–term gene expression and phenotypic correction using adeno–associated virus vectors in the mammalian brain. Nature Genetics, 8:148–153.

Lindvall, et al. 1989. Human fetal dopamine neurons grafted into the striatum in two patients with severe Parkinson's Disease. Arch. Neurol., 46:615–631.

Lo, et al. 1999. Adeno–associated virus–mediated gene transfer to the brain: Duration and modulation of expression. Human Gene Therapy, 10:201–213.

McCown, et al. 1997. Inferior collicular seizure generalization produces site–selectrive cortical induction of cyclooxygenase 2 (COX–2). Brain Research, 767:370–374.

Widner, et al. 1992. Bilateral fetal mesencephalic grafting in two patients with Parkinsonism induced by 1–methyl–4–phenyl–1,2,3,6–tetrahydropyridine (MPTP). The New England Journal of Medicine, 327(22):1556–1563.

* cited by examiner

ANTIBIOTIC INDUCIBLE/REPRESSIBLE GENETIC CONSTRUCT FOR GENE THERAPY OR GENE IMMUNIZATION

CROSS-REFERENCE TO RELATED APPLICATIONS

This application claims priority to United States Provisional Application Ser. No. 60/150,484 filed on Aug. 24, 1999, the disclosure of which is incorporated herein by reference in its entirety.

FIELD OF THE INVENTION

The present invention is in the field of biotechnology and is related to a new antibiotic inducible/repressible genetic construct or system for improving particle the control of gene therapy or gene immunization. In particular, a system or genetic construct adapted for all types of gene therapy and gene immunization based upon the use of naked DNA or DNA incorporated into various vectors (such as plasmide, adeno-associated viruses, autonomous parvoviruses, retroviruses or adenoviruses or a combination thereof).

BACKGROUND OF THE INVENTION

Various systems comprising naked DNA or DNA incorporated into a suitable vector (plasmid, virus, cationic visicule, . . . ) are used in gene therapy or gene immunization (vaccine). Various publications describe for gene transfer into cells, the use of adeno-associated viruses, which are human defective parvoviruses whose genomes are made of single stranded DNA molecules. Six or five different serotypes have been cloned in prokaryotic plasmide and could be used to derive vectors.

The international patent application PCT/US95/04587 describes gene delivery to adult CNS using AAV vectors.

Humans suffering from Parkinsonism have been treated by striatal implantation of foetal dopaminergic neurons (Lindvall et al., Arch. Neurol. 46:615–631 (1989); Widner et al. New Engl. J. Med. 327: 1556–1563 (1992). Following surgery, the patients exhibited improvement of neurological function. Grafts partially re-establish dopaminergic activity and ameliorate motor functions. However, the success of foetal brain tissue transplantation into impaired area of Parkinson's and Huntington's patients brain is limited by the poor survival of the graft. To ensure maximal viability, the foetal tissue must be freshly harvested prior to transplantation. Recent advances consist of keeping the tissue refrigerated (at 4° C.) for 24 hours without loss of viability. Nevertheless, the coordination between the harvesting of the foetal tissue and the transplantation procedure is still a problem. Furthermore, the amount of foetal tissue available for transplantation is limited for practical and ethical reasons. Foetal tissue is technically difficult to obtain, particularly if multiple donors are needed for each patient. This limits the widespread applicability of foetal tissue transplantation.

The supply of Glial cell line-Derived Neurotrophic Factor (GDNF), a neurotrophic factor for dopaminergic neurons, could promote the protection of rafted cells as well as of remaining host dopaminergic cells. However, since neurotrophic factors can not cross he brain-blood-barrier, they have to be administrated directly in the brain in sustained levels.

The international patent application (PCT)/US96/05814 describes a method of using neurotrophic actors to enhance neuronal survival and promote functional integration of grafted neurons using osmotic umps implanted in the brain. This technique is difficult to implement in the clinics, in particular because of the risk of bacterial contamination.

Improving the survival of the grafted tissue by transfer of genes coding for neurotrophic factors would reduce the amount of tissue needed per patient and make the transplantation therapy available to a greater number of patients.

Stable genetic modification of the graft cells by the means of viral vectors expressing trophic factors could be used to enhance the survival of the grafted tissue.

Genetically-modified foetal mesencephalon fragments or dissociated cell suspensions expressing GDNF could be grafted in order to obtain i) a better survival of the graft (autocrine effect), ii) the protection of host's dopaminergic terminals in the putamen and of a dopaminergic cell bodies in the substantia nigra after retrograde transport of GDNF (paracrine effect).

Furthermore, the combination of autocrine and paracrine effects could result in a better correction of parkinsionnian symptoms by foetal grafts transplants.

Adeno-associated virus is a human defective parvovirus whose genome is a single stranded DNA molecule. Five different serotypes have been cloned in prokaryotic plasmide and could be used to derive vectors.

For efficient replication AAV requires a co-infection with a so-called "helper virus", usually adenovirus or herpes simplex virus. In the absence of helper virus, AAv can still enter host cells but it stays latent with his genome integrated in the cellular genome. The genome is flanked by 2 inverted terminal repeats (ITRs) which serve as a replication origin.

The double-stranded form of AAV type 2 has been cloned in a pBR322 plasmid allowing the genetic analysis of the virus as well as the development of vectors for gene transfer (Samulski et al. 1982).

It was soon realized the non-coding ITRs are the only elements required in cis for replication and encapsidation of the viral genome (McLaughlin et al., 1987). Accordingly, the vectors derived from AAV only retain the ITRs; the internal coding region is replaced by the desired transgene(s) and regulatory elements (Samulski et al. 1989). To produce recombinant viral particles, a plasmid containing the ITRs flanking the transgene expression cassette is transfected into producer cells in which AAV rep and cap genes as well as necessary helper virus genes are provided either by transfection or by infection.

AAV vectors transduce various types of neurons in the adult rat (McCown et al., 1997, Klein et al., 1998) and monkey (During et al., 1998) as well rodent and human neurons in culture (Du et al., 1996). Human brain slices from epileptic patients could also be transduced by AAV vectors (Freese et al., 1997). AAV vectors were shown to integrate in neurons (Wu et al., 1998).

The international PCT/US95/04587 describes gene delivery to adult CNS using AAV vectors.

However, controllable gene expression is a prerequisite for safe gene therapy or gene immunization in many protocols: for example, erythropoietin level is critical for the treatment of β-thallaseemia.

In models for Parkinson's disease, the intrastriatal delivery of AAV viral vectors encoding GDNF resulting in long-term overexpression of GDNF effectively protects dopaminergic neurons but also results in side-effects on neighboring normal cells (Kirik et al., 2000). PCT/US94/06734 describes a prokaryotic tetracycline system to produce a genetic switch for achieving control of eukaryotic gene expression. In the native prokaryotic tetracycline system, tetracycline is an effector that induces prokaryotic gene expression by binding to a tetracycline repressor protein. In the absence of tetracycline, the tetracycline repressor binds to a tetracycline operator sequence, which is linked to a promoter and represses transcription. In the presence of tetracycline, the tetracycline repressor binds tetracycline, which binding displaces the repressor from the tetracycline operator sequence , so repression is relieved and transcription can begin.

This tetracycline-controlled activator system is constructed by fusing a tetracycline repressor to a transcription activation domain from a protein that activates transcription in eukaryotic cells. In the absence of tetracycline, the tetracycline-controlled activator (tTa) binds the tetracycline operator sequence which is linked to a promoter and activates transcription. In the presence of tetracycline, the tetracycline-controlled activator binds tetracycline, which binding displaces the activator from the tetracycline operator sequence so activation is ended and transcription is silenced. This is a tetracycline-repressible system.

In a further adaptation, the tetracycline-transactivator is mutated in such a way that it binds the tetracycline operator sequence only when tetracycline binds to the mutant tetracycline transactivator (rtTA). Consequently, in the absence of tetracycline, transcription does not occur. In the presence of tetracycline, transcription can begin. This is a tetracycline-inducible system.

These regulatory systems require that two different expression vectors enter each cell. A first expression vector encodes the tetracycline-controlled activator. A second expression vector encodes the desired transgene under the control of the tetracycline operator sequence linked to a promoter.

However, the probability of transfecting a single cell with two plasmid DNAs is significantly lower than for transfecting that cell with one plasmid DNA. Furthermore, it is important for regulation of expression that the two constructs are present in the optimal ratio.

The U.S. Pat. No. 5,891,718 patent describes a self-accelerating plasmidic system inducible by tetracycline and its analogs, using 2 genes (tTA or rtTA and the gene of interest) expressed from the same tetracycline-inducible/repressible promoter and separated by an "Internal Ribosome Entry Site" (IRES).

This one-plasmid system inducible by tetracycline was shown to be suitable for transient expression in muscle. However, naked DNA is not effective in gene transfer in other organs, for example in the brain. Furthermore, naked DNA does not seem to be effective for long-term gene expression.

In contrast, AAV vectors are effective in long-term gene delivery and expression, in particular in the brain, muscle and liver.

Furthermore a self-accelerating system is based on low level background expression of the tetracycline transactivator and concomitantly of transgene resulting from the basal activity of the minimal CMV promotor (which is part of the tetracycline-responsive element). Therefore, this system is by essence leaky.

Accordingly, the U.S. Pat. No. 5,891,718 patent describes 40-fold induction of transgene in vivo in the muscle. However, background expression in the absence of tetracycline is still detectable in this system.

Bohl et al. (1998) describe a AAV vector expressing erythropoietin (EPO) under a tet-repressible promoter. After injection in the muscle, in the presence of tet EPO is expressed, in the absence of tet EPO is expressed at reduced level but still significantly higher, than the background level. In this construct, the reverse tetracycline transactivator (rtTA) is under the control of a constitutive retroviral promoter and EPO is under the control of tetracycline operator (tetO) sequences linked to a minimal CMV promoter (miniCMV). In this system the expression of the EPO transgene is induced ~10 fold in response to doxycylin.

Haberman et al. (1998) describe a AAV vector expressing gfp under a tet-repressible promoter. This is a single construct with tTA under control of tetO miniCMV and the reporter gene coding for "green fluorescent protein" (gfp) under the control a second tetO miniCMV. Thus this is a self-accelerating system After infusion in the brain, in the absence of tet, gfp is expressed; in the presence of tet gfp is expressed at reduced level but still significantly higher than the background level. In this system, the addition of tetracycline results in a ~15-fold reduction of gfp expression.

The presence of a high background level of transgene expression in these two systems could originate from 2 difficulties.

i) Flotte et al. (The Journal of Biol. Chem. 268, 3781–3790, 1993) showed that AAV ITRs have a promoter activity. Thus , in the constructs by Bohl et al. and Haberman et al. tet-independent transcription of gfp can occur from AAV ITRs.
ii) The enhancer elements present in the retroviral LTRs are acting at distance and in both orientations.

Paulus et al. (J. Virol. 70, 62–67, 1996) describe a retroviral vector which proposes a solution for problems n°i) and ii):

They constructed a LTR-TRE-lacZ-IRES-tTA vector in which: "potential cis-regulatory problems in the tetracycline regulation of the phCMV-1 promoter due to proximity to potent Moloney viral enhancer and promoter elements are eliminated by the use of a SIN vector which lacks these elements".

Flotte et al. (ref) showed that AAV ITRs have a promoter activity. Thus , tet-independent transcription of gfp can occur from AAV ITRs.

AIMS OF THE INVENTION

The present invention aims to provide a new inducible/repressible genetic construct and a vector comprising it, which do not present the drawbacks of the state of the art and which improve the control of the expression of gene(s) of interest, especially in the field of gene therapy and gene immunization.

A preferred aim of the invention is to provide a single self-accelerating AAV viral vector that contains all the elements necessary for a tight regulation on a single construct smaller than 4.7 kb which can be encapsidated using plasmids expressing capaids from AAV-2 or AAV5 and required adenoviral genes.

A further aim of the invention is to provide strong transcription termination insulating the ITRs from the transgenes and consequently avoiding tet-independent transcription.

It is also an aim of the invention to reduce background expression of the transgene due to basal activity of the bidirectional tetracycline-inducible promoter to level undetectable using quantitative methods known by the one skilled in the art (for example: ELISA, fluorimetry, spectrophotometry, etc.).

SUMMARY OF THE INVENTION

Figure 6:
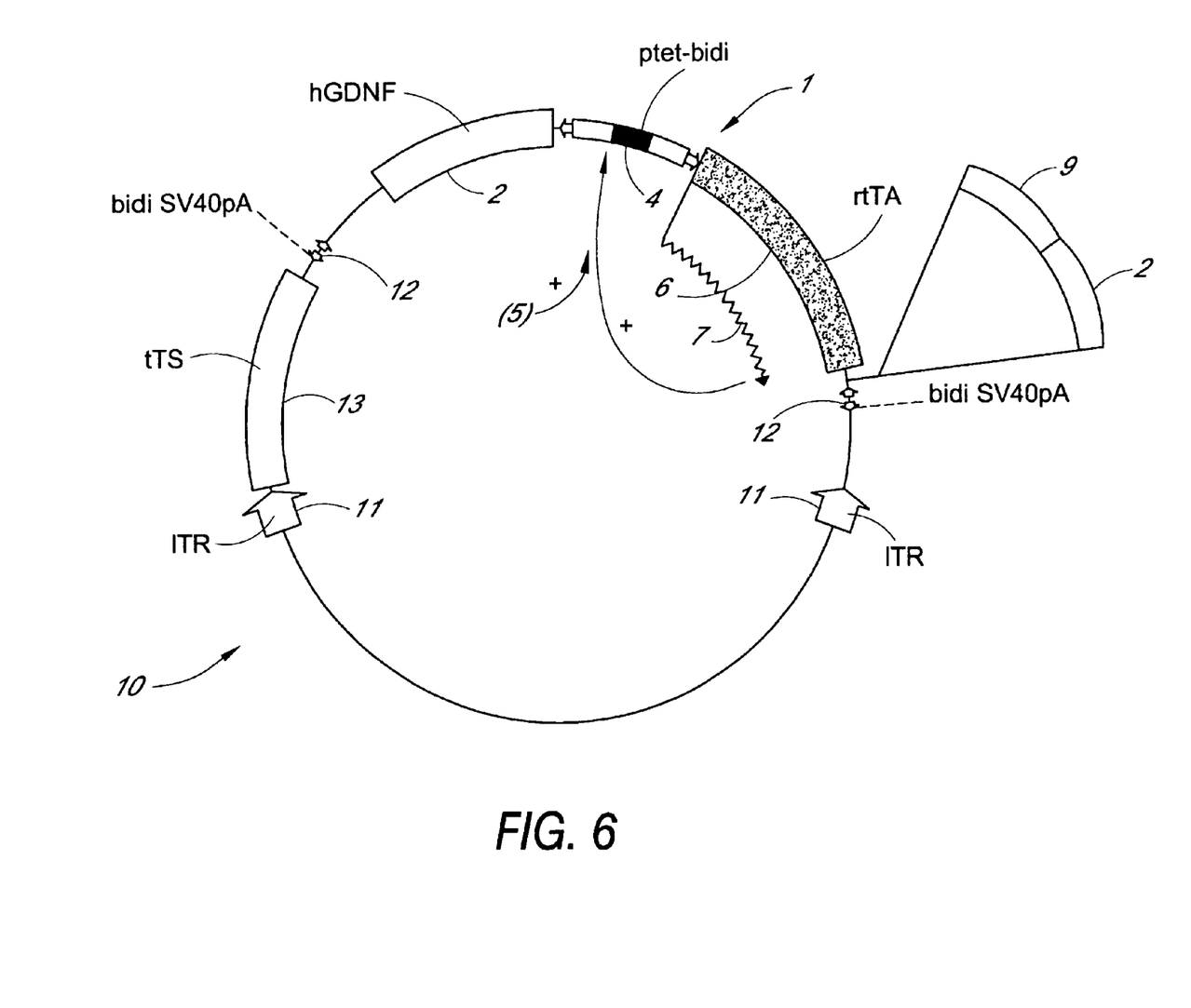
FIG. 6 shows an antibiotic inducible/repressible genetic construct and the vector comprising the construct.

The present invention is related to an antibiotic inducible/repressible genetic construct (or system) for improving the control of gene therapy and gene immunization and which (by the administration of said antibiotic 5 to a patient) induces the transcription and the expression of one (or more) gene(s) of interest incorporated in said genetic construct by a transfected cell or tissue. According to the invention, said genetic construct 1, controlling the transcription of the gene of interest 2 by said cell 3, comprises a bi-directional antibiotic controlled activator-responsive promoter/operator sequence 4 located between (and controlling the transcription of) the gene of interest 2 (or an insertion site for said gene of interest 2) and a cistron 6, encoding a reverse antibiotic controlled traneactivator 7. In said construct or system the bi-directional antibiotic controller activator responsive promoter/operator sequence 4 is advantageously activated by the transactivator factor 7, encoded by the reverse antibiotic controlled transactivator nucleotide sequence 6 in the presence of said antibiotic 5 (see FIG. 6).

Advantageously, the antibiotic elements used according to the invention is the tetracycline or its analogue (such as doxycyclin) and the reverse antibiotic controller activator is a reverse tetracycline controlled traneactivator (rtTA), whose sequence has been described by Goossen et al., Science, Vol. 278, p. 1766–1769 (1995) and preferably obtained from the Clontech Laboratories catalogue.

Preferably, the bi-directional antibiotic controller activator responsive promoter/operator sequence 4 comprises, located between two mini CMV-promoter, an antibiotic responsive element, preferably a tetracycline responsive element (TRE), consisting of 7 copies of the 42 base pairs of the tetracycline operator sequence, such as the one described by Baron U. et al., Nucleic acid research, Vol. 17, p. 3605–3606 (1995).

Such bi-directional sequence (Pbi-1) is described in the Clontech Laboratories catalogue.

The genetic construct 1 further comprises (preferably bi-directional) terminator sequences such as (SV40 poly-A) poly-adenylation sequences 12 at its both extremities.

Advantageously, the gene construct 1 according to the invention further comprises downstream the antibiotic controlled transactivator sequence 6, another cistron comprising one (or more) gene(s) of interest 2 (or integration site of one (or more) gene(s) of interest 2) and an internal ribosone entry site (IRES) 9 positioned between said gene of interest 2 or integration site of gene of interest and the second nucleotide sequence 6, encoding the reverse antibiotic controlled transactivator 7.

It is meant by a site of integration of a gene of interest 2, a specific genetic sequence (such as polylinker or a genetic sequence comprising a unique restriction enzyme site) allowing the incorporation of a (foreigner) gene of interest 2 incorporation in the genetic construct 1 according to the invention.

Another aspect of the present invention is related to a vector 10 comprising the genetic construct 1 according to the invention. Preferably, said vector is selected from the group consisting of plasmids, viruses, cationic vesicles or a mixture thereof. Advantageously, the vector 10 comprises the genetic construct 1, disposed between two terminal encapsidation, integration and replication viral genetic sequences 11, preferably between two adeno-associated viral (AAV) or adeno-viral ITR-sequences, two retro-virus LTR-sequences or two palindromic sequences of an autonomous parvovirus.

Preferably, the vector 10 according to the invention comprises also between the genetic construct 1 and said terminal sequence 11, two SV40 bi-directional poly-adenylation (Poly-A) sequences 12.

Furthermore, the nucleic acid construct 1 or the vector 10 according to the invention comprises advantageously a sequence encoding an antibiotic silencer sequence 13 located between the viral terminal sequences 10 and the (bi-directional) SV40 poly-adenylation sequences 12.

In the genetic construct 1 according to the invention, the genes of interest 2 are advantageously therapeutic genes, preferably selected from the group consisting of anti-apoptotic sequences (such as bel-2), sequences encoding neurotrophic factors, preferably GDNF, BDNF, NT4 or CNTF, genetic sequences encoding protein such as erythropoietin (EPO), a human growth factor, a tissue granylocyte macrophage colony stimulator factor (GM-csF), tissue plasminogen activator (tPA), coagulation factors (FVIII, FIX), insulin, calcitonyn, thimidine kinase, interleukins (IL-2, IL-6, ... ), interferons ($\alpha$, $\beta$, $\gamma$), tumor necrosis factor, genes encoding enzymes involving the detoxification of free radicals (such as superoxide dismutase or the genetic sequence described in the document PCT/BE98/00124, incorporated herein by reference), genetic sequences encoding tumor-specific antigens such as antigens MAGE 1, MAGE 3, etc.).

Another aspect of the present invention is related to a cell (including stem cells) and/or tissue (preferably a mesencephalic tissue or a striatal tissue) transformed by the genetic construct or the vector according to the invention, preferably a cell which could be used also as a cellular vector or a vaccine for genetic and/or cellular therapy and immunization. Preferably, said genetic therapy using the nucleic acid construct or vector according to the invention allows a transformation of cells obtained from foetal-nervous tissues which are thereafter used for the treatment of neurodigenerative diseases, especially for the treatment of Parkinson disease, Alzheimer or Huntington disease.

Another aspect of the present invention is related also to a method for improving the survival of graft of foetal-nervous tissue by inducing a genetic modification in the cell(s) of said tissue with a viral vector (preferably a AAV-vector, more preferably the vector according to the invention) encoding a neurotrophic factor for improving the treatment of neuro-degenerative diseases, especially Parkinson disease (using for example GDNF) and Huntington disease (using for example CNTF).

More preferably, said neurotrophic factor is the one described above.

BRIEF DESCRIPTION OF THE DRAWINGS

FIGS. 1A and 1D show cells detected by native fluorescence, FIG. 1B shows cells detected by immunofluorescence and FIG. 1C shows cells detected by immunocytochemistry. Foetal samples were fixed 3 days (B), 7 days (C), or six weeks (A and D) post-infection and frozen.

DETAILED DESCRIPTION OF THE INVENTION

The inventors have discovered that it is possible to obtain an early and sustained gene transfer into human foetal-nervous tissues by using an AAV-vector, preferably the vector according to the invention.

In this method, tissue fragments rather than dissociated cells are incubated in a viral suspension. AAV vectors expressing the gfp reporter gene transduce human foetal brain tissue with a high efficiency at least for 3 days (the earliest time point tested) to 6 weeks (the latest time point tested).

Unexpectedly, an AAV vector carrying the gene coding for GDNF under the control of an inducible promoter, for example the inducible promoter could be used to transduce human foetal brain tissue prior to transplantation in order to be able to control the amount of GDNF delivered by the grafted tissue.

A similar strategy could be used for the treatment of other neurodegenerative disease, such as e.g. Huntington's disease, using grafts of striatal tissue and an appropriate neurotrophic factor, for example CNTF.

AAV vectors do not express any viral gene and present a minimal risk of immune rejection. Antibodies against AAV capsid have been detected after injection of recombinant virus, however, without concomitant reduction in the number of transduced cells (Lo et al. 1999 ). In the strategy proposed here, foetal tissue is infected ex vivo before transplantation. Washing the tissue to eliminate the excess of virus which did not enter the cells reduces the risk of raising antibodies against capaid proteins by the transplanted host.

In order to obtain a single self accelerating AAV-vector that contains all the elements necessary for tight regulation on a single small construct, the inventors have prepared a genetic construct comprising a bi-directional promoter which drives the transcription of tTA and a gene of interest (GFP or GDNF). This construct is advantageous, because it is small and can be easily encapsidated by using plasmid expressing AAV rep and cap genes and required adenoviral genes.

The construct according to the invention comprises a bi-directional transcription terminal signal (poly-A) located at its both ends (of tTA and of the gene of interest) which provide strong transcription termination insulating the ITRs from transgene and consequently, avoid tet-independent transcription. In addition, the introduction of a transcription silencer sequence (tTS) placed downstream to the ITRs of the virus, provide a constitutive low-level transcription of the tetracycline silencer which reinforces the control of the transgene expression and therefore reduces background expression of said gene of interest due to basal activity of the bi-directional tetracycline inducible promoter/operator sequence to undetectable level (by elisa, fluorimetry, spectrophotometry, etc.).

The tTS sequence consists of a fusion between the procaryotic tetracycline repressor and the silencer domain of the kid-1 eucaryotic transcription factor (Witzgall et al., PNAS 91, p; 4514–4518 (1994)). In this system in the absence of tetracycline, the tetracycline traneactivator does not bind to the tetracycline operator sequence, whereas, the tetracycline silencer binds to the tetracycline operator sequence and blocks transcription. In the presence of tetracycline, the tetracycline transactivator binds to the tetracycline operator sequence and activates transcription whereas the tetracycline silencer detaches from the tetracycline operator sequence.

The present invention would be described in detail in the following examples, which are presented as non-limited illustrations of the various aspects of the present invention.

EXAMPLE 1

Infection of Human Foetal Mesencephalon with AAV-CnV-EGFP

An AAV vector expressing the EGFP gene under the control of the CMV promoter can transfer and express the transgene as early as 3 days and at least until 6 weeks after infection of human foetal mesencephalon. (see FIG. 1). A total of 4 human embryos were infected and gfp expression analyzed.

Embryo 1: 8 weeks of gestation
Embryo 2: weeks
Embryo 3: weeks
Embryo 4: 7 weeks of gestation.

Figure 1A:
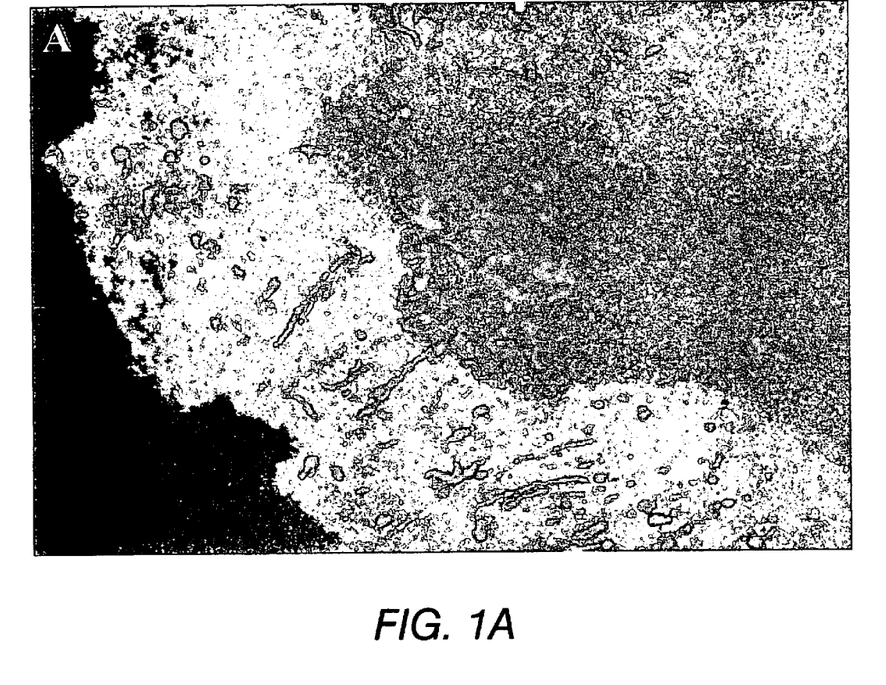
FIGS. 1a–1d show detection of transduced human foetal mesencephalon cells expressing EGFP from a vector of the present invention.
Figure 1B:
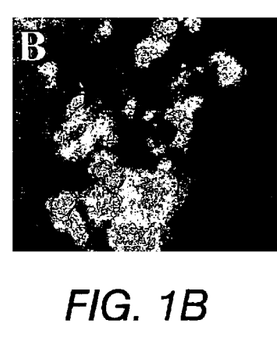
Figure 1C:
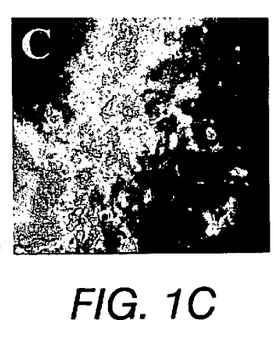
Figure 1D:
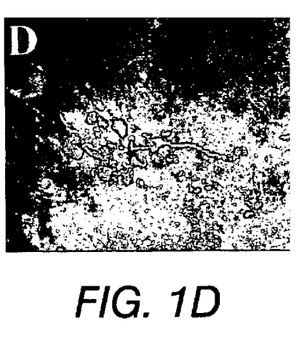

The transduced cells were detected i) by native fluorescence (FIGS. 1A§D, embryos #2&3) ii) by immunofluorescence (FIG. 1B; embryo #1) iii) by immunocytochemistry (FIG. 1C; embryo #4). The mesencephalon was isolated from the rest of the embryo according to (Björklund and Dunnett eds. Neural Transplantation, a practical approach).

In a specific embodiment of the invention, small fragments (12 per mesencephalon) are incubated in a viral suspension consisting in either a concentrated purified viral stock-see below) or a purified viral stock diluted in HBSS:organotypic medium (1:1).

After 2 hours to allow viral adsorption and internalization, the fragments were either put in organotypic cultures or dissociated by trypsin and cultured as adherent cells on poly-L-lysin coated slides, a method which allows to select neurons.

In another embodiment, large fragments (half-mesencephalon) are put in organotypic culture and a small volume of a concentrated purified viral stock is injected using a Hamilton syringe.

Organotyplc Cultures of Human Foetal Brain

Mesencephalon or adjacent tissue from human embryos (6 to 9 weeks of gestation) was dissected. Large fragments (embryo#1) or small fragments (embryos 2§3) were placed in Tranowells (Costar). The lower compartment contained 1 ml of MEM medium supplemented with 25% horse serum, hepes 15 mM, HBSS 25%, glucose 2%, glutamine, $NaHCO_3$ 3.7%, penicillin, streptomycin ("organotypic medium)". The cultures were maintained at 35° C. in a humidified atmosphere with 5% $CO_2$.

Cultures of Human Embryonic Neurons

Infected fragments of mesencephalon were dissociated by trypein and cultured on squared poly-L-lysin (Sigma)-coated slides (6.25 cm2). (3 slides for one mesencephalon). The cultures were maintained in organotypic medium for 3 days, allowing specific attachment of neurons, for 4 days before fixation with 4% paraformaldehyde.

Plasmids

The AAV vector plasmid pTR-EGFP expressing the EGFP reporter gene (Clonetech) under the control of the CMV promoter, has been described elsewhere (Tenenbaum et al., 1999).

Production and Purification of Recombinant AAV Virus

Procedure I

Recombinant rAAV-CMV-EGFP virus was obtained as previously described (Tenenbaum et al., 1999). Briefly 293/T cells were co-transfected with pTR-EGFP and pIM45, a plasmid expressing AAV viral genes, cells were infected with adenovirus-2 24 hours post-transfection and harvested 54 hours post-infection. Cesium-chloride purified rAAV-EGFP viral suspension was prepared as previously described.

Procedure II

Recombinant rAAV-EGFP and rAAV-CMV-rGDNF virus were obtained as follows. 293/T cells were co-transfected with pTR-CMV-EGFP or pTR-CMV-rGDNF and pDG, a plasmid expressing AAV viral genes and required adenovirus genes and harvested 52 hours post-transfection. The rAAV viral preparation was purified by iodixanol gradient followed by heparin agarose column according to Zolotukhin et al. (1999, Gene Ther. 6)

Fluorescence Activated Cell Sorter (FACS) Analysis

Ten thousand cells were analyzed using a Becton Dickinson FACS scan and the Lysis II software. The statistical analyais of the data was performed using the WINMDI program and the dot-plot option.

Titration of rAAV-EGPP Virus by FACS Analysis

Fifty-thousand 293/T cells per well were seeded in 24 wells plates, 1 day before infection. Cells were infected with dilutions of the rAAV-EGFP preparations in 1 ml of serum-free medium containing $10^5$ pfu of wild-type adenovirus. The number of green fluorescent cells expressing the EGFP gene was evaluated 2 days after infection by FACS analysis of $10^4$ cells.

The percentage of fluorescent cells was used to calculate the titer of the rAAV-EGFP viral preparation (expressed in transducing units per ml) as follows:

$$\frac{5 \; 10^4 \times \text{percentage of fluorescent cells}}{100 \times \text{dilution of } rAAV}$$

Immunofluorescence

Gfp-immunoflurescence on brain sections: Foetal samples were washed with PBS at 35° C. for 15 min., then 4% paraformaldehyde in PBS at 35° C. was carefully added on the sample and the plates were further maintained at 35° C. for 15 min. The samples were post-fixed in 4% paraformaldehyde at 40° C. overnight, then rinsed with PBS and immersed in PBS 20% sucrose 4% paraformaldehyde overnight. The samples were frozen in a mixture of isopentane and dry ice 30 seconds at −20° C., 10 seconds at −30° C. and for overnight at −80° C.

Twenty micron cryostat sections were labeled in liquid ("free-floating" method) as follows. Sections were sequentially incubated in: i) THST (50mM Tris, 0.5 M NaCl, 0.5% triton X100 pH7.6) for 30 min.; ii) polyclonal rabbit anti-gfp (Clonetech) diluted 1:250 in THST overnight at 4° C.; iii) donkey anti rabbit-biotin (Amersham) 1:200 in TBS, 1 hour at room temperature; iv) streptavidin coupled with fluorescein, 1:100 in TBS. Sections were mounted on gelatin-coated slides, dehydrated and mounted using Vectashield mounting fluid for fluorescence (NTL laboratories).

Sections were photographed using a Zeiss Axiophot 2 microscope equipped with a U.V. lamp and an FITC filter.

RESULTS

Injections of rAAV-EGFP in brain slices.

Experiment 1: Roughly circular pieces of human foetal cerebral trunk, adjacent to the ventral mesencephalon, with a surface of approximately 5 mm² and thickness of approximately 200 µm were maintained in Tranuwells at 35° C., 5% $CO_2$ for 4 hours before infection. Two injections of 1 µl of rAAV-EGFP (prepared according to procedure I) containing $1.2 \; 10^5$ transducing units were performed. PBS was infected in control samples. The first injection was performed transversal to the plan of the sample, while the second injection was performed perpendicularly to the sample in its middle. A 10 µl Hamilton seringe connected with a 26 G needle was used. Injections were performed manually with a speed of 0.2 µl/minute. The needle waoowithdrawn carefully and slowly. The infected tissue was further cultured for 6 weeks, while replacing half of the medium (0.5 ml) by fresh medium twice a week.

Experiment 2: Small fragments of human foetal mesencephalon (0.1–1 mm³) were incubated in 96 wells plates in 20 µl of a 1:1 mixture of a viral suspension in PBS (containing $3 \times 10^6$ T.U) and organotypic medium. The rAAV-EGFP stock used was prepared according to procedure I and had titer of $3 \times 10^8$ T.U./ml.

After 2 hours at 37° C., the tissue fragments were transferred to Transwells and maintained in culture at 37° C. as described above.

Experiment 3: Small fragments of human foetal mesencephalon (0.1–1 mm³) were incubated in 96 wells plates in 20 µl of a 1:9:10 mixture of a viral suspension in PBS (containing $1.7 \times 10^6$ T.U): organotypic medium: HBSS. The rAAV-EGFP stock used was prepared according to rpocedure II and had titer of $1.7 \times 10^9$ T.U./ml.

After 2 hours at 37° C., the tissue fragments were dissociated by trypsin and the cell suspension plated on poly-L-lysin coated slides in serum containing ("organotypic") medium. Three days later, the medium was replaced by serum-free medium and the culture was maintained further for 4 days.

AAV-Mediated Geneo Tranafer in Human Footal Mesencophalon

Experiment 1; Six weeks post-injection the samples were fixed and frozen sections were labeled using anti-gfp antibodies. FIGS. 1A & D shows that numerous cells with a neuronal morphology appeared. The transduced area covered approximately one third of the sample. A smaller area of transduced cells also appeared in the middle of the sample (FIG. 1D), possibly corresponding to the injection that was performed perpendicularly to the slice.

Experiment2: Three days and 2 weeks post-injection, the samples were fixed and.frozen sections were observed under fluorescence microscopy to detect native gfp fluorescence. FIGS. 1B & C shows that labeled cells appeared 3 and 7 days post-infection, respectively. At three days, the cells had the morphology of poorly differentiated neurons with very few and short processes. At 7 days, additional processes appeared, suggesting that rAAV-mediated gene transfer does not interfere with the differentiation of neurons in organotypic culture.

Foetal samples were fixed 3 days (B), 7 days (c) or 6 weeks (A & D) post-infection and frozen. A & D: Twenty micron cryostat sections were immunolabelled as described in Material and Methods. B & C: Fragments were examined by fluorescence microscopy to detect native fluorescence.

Figure 2A:
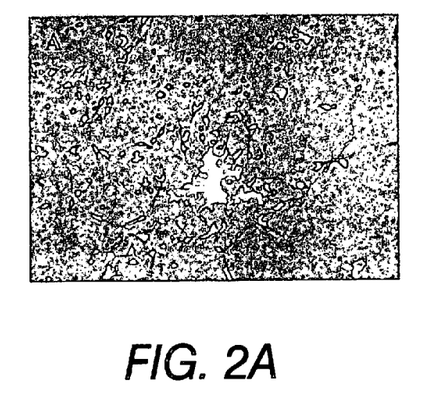
FIGS. 2a–2b show human foetal mesencephalon cells 7 days post-infection which were transduced with a vector of the present invention and evaluated with anti-tyrosine hydroxylase (TH) or anti-gfp polyclonal antibodies. Recombinant AAV-infected fragments of human VM were dissociated and cultured on poly-L-lysine coated coverslips. After 7 days, attached cells were fixed and processed for gfp-(A) or TH-immunocytochemistry.
Figure 2B:
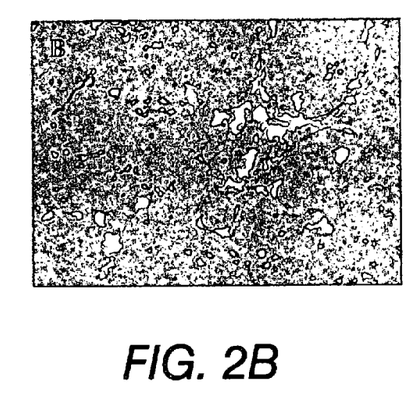

Experiment 3: 7 days after infection, the cultures were fixed and labeled using anti-gfp polyclonal antibodies or anti-tyrosine hydroxylase polyclonal antibodies (FIG. 2) or counterstained with hematoxylin to evaluate the total number of cells in the culture.

EXAMPLE 2

Infection of Rat Foetal Mesencephalon with AAV-CKV-EGFP

We found that an AAV vector expressing the EGFP gene under the control of the CMV promoter can transfer and express the transgene as early as 4 days and at least until 3 weeks after infection of rat foetal mesencephalon.

A total of approx. 100 rat embryos were used either non-infected, infected with AAV-CMV- Egfp or with AAV-CMV-rGDNF.

The transduced cells were detected i) by native fluorescence ii) by FACS analysis of dissociated cells iii) by immunocytochemistry.

In a specific embodiment of the invention, small fragments (12 per mesencephalon) are incubated in a viral suspension as described in example 1.

The AAV vector plasmid expresses the rat GDNF cDNA and expresses the rat GDNF under the control of the CMV promoter. The cDNA coding for rat GDNF was obtained by RT-PCR using mRNA from lesioned sciatic nerve and the following primers: 5'ATGAAGCTTGGTCTAC-GGAGACCGGATCCGAGGTGC_3'(SEQ ID NO: 1) and 5'GGTCTAGATCTCTGGAGCCAGGGTCAGATACAT-C3'(SEQ ID NO: 2).

The PCR fragment was digested by HindII and XbaI cloned in pTR-EGFP.

The resulting clones were sequenced and one clone with a sequence corresponding to rat GDNF cDNA (described in . . . ) was retained.

GDNF expressed by this plasmid after transfection of 293/T cells was measured by ELISA.

ELISA test

Recombinant rAAV-EGFP and rAAV-GDNF virus was obtained as follows. 293/T cells were co-transfected with pTR-EGFP and pDG and harvested 52 hours post-infection. The viral suspension were purified by iodixanol gradient followed by heparin agarose column purification as described by Zolotukhin et al. (1999).

Fluorescence activated cell sorter (FA CS) analysis

Ten thousand cells were analyzed using a Becton Dickinson FACS scan and the Lysis II software. The statistical analysis of the data was performed using the WINMDI program and the dot-plot option.

Titraeton of rAAV-ZP Virus by FACS Analysis

Fifty-thousand 293/T cells per well were seeded in 24 wells plates, 1 day before infection. Cells were infected with dilutions of the rAAV-EGFP preparations in 1 ml of serum-free medium containing $10^5$ pfu of wild-type adenovirus. The number of green fluorescent cells expressing the EGFP gene was evaluated 2 days after infection by FACS analysis of $10^4$ cells.

RESULTS

Small fragments of rat foetal mesencephalon (12 per mesencephalon) were incubated in Eppendorf tubes in 20 µl of a 1:9:10 mixture of a viral suspension in PBS IM NaCl (containing $1.7 \times 10^6$ T.U): organotypic medium HBSS. The rAAV-EGFP stock used had titer of $1.7 \times 10^9$ T.U./ml. After 2 hours at 37° C., the tissue fragments were either:
i) put in organotypic cultures. GFP expression was evaluated either by fluorescence microscopy or by FACS analysis after trypsin dissociation.
ii) dissociated by trypsin and the cell suspension plated on poly-L-lysin coated slides in serum containing ("organotypic") medium. Three days later, the medium was replaced by serum-free medium and the culture was maintained further for 4 days.

AAV-mediated Gene Transfer in Rat Foetal Memencephalon

Experiment 1: 2 days to 3 weeks poet-injection the samples were fixed and examined under fluorescence microscopy. This shows that cells with a neuron morphology appeared at 4 days from infection. The transduction efficiency was significantly lower than when using human tissue.

Figure 3A:
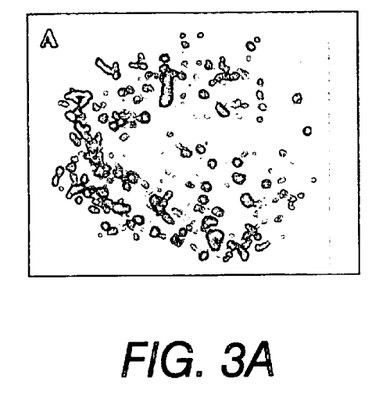
FIGS. 3a–3b show rat foetal mesencephalon cells transduced with a vector of the present invention. Fragments of rat foetal mesencaphalon were incubated with 1.5×10$^6$ T.U. of rAAV-EGFP and maintained in organotypic cultures.
Figure 3B:
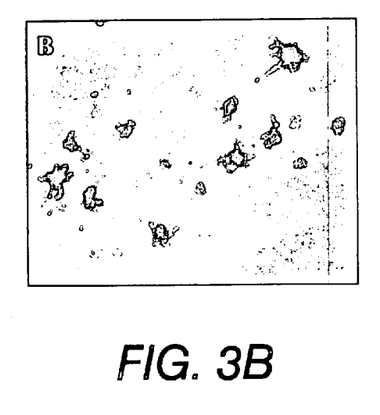

Experiment 2: Three days to 1month post-infection, the samples were dissociated by trypsin and analyzed by FACS The percentage of gfp-positive cells was low (0.1–0.5%) but stable from 4 days to 1 month post-infection (FIG. 3).

Experiment 3: Rat embryonic mesencephalons were infected either with rAAV-CMV-EGFP or with rAAV-CMV-GDNF and put in organotypic culture. After 3 weeks, the cultures were fixed and immunohistochemistry for dopamine was performed. The density of dopaminergic fibers was higher (A2D) and the dopaminergic cell bodies were larger C2D when the tissue was infected with RAAV-CMV-GDNF than with rAAV-CMV-EGFP.

Experiment 4: Rat embryonic mesencephalons were infected either with Raav-cmv-egfp or with rAAV-CMV-GDNF. 7 days after infection, the cultures were fixed and incubated with hoechst to detect apoptotic nuclei and labeled using anti-tyrosine hydroxylase polyclonal antibodies followed by a secondary antibody coupled with texas red.

Experiment 5: Embryo fragments were infected with rAAV-CMV-EGFP, dissociated with trypsin and transplanted in the striatum of adult rats.

Three weeks and 3 months after transplantation, the rate were sacrificed and frozen brain section were submitted to gfp immunohistichemistry.

Three weeks after transplantation, the grafts were clearly visible in the striatum and GFP-positive cells could be detected in the grafts.

EXAMPLE 3

Doxycycline-inducible Expression of gfp or GDNF Mediated by an AAV Vector

Material and methods
Plasmids
The minimal CMV promoter is the core immediate early promoter of the human cytomegalovirus, in which the enhancer sites have been deleted.

The bidirectional promoter consists of 2 minimal CMV promoters linked by tetracycline operator sites and is located in the middle of the vector.

Starting from the middle, the right open reading frame directs the transcription of the tTA tetracycline activator consisting in the tetracycline repressor DNA-binding domain fused to the transcription activation domain of the herpes simplex virus VP16 protein.

Also starting from the middle, the left open reading frame directs the transcription of the gfp gene.

Transcription of both cassettes ends at the SV40 bidirectional transcription termination signal.

PTR-tTS-tetON-tTA-EGFP plasmid contains in addition to the 2 cassettes directing the transcription of tTA and EGFP from the bidirectional tetO-miniCMV promoter, the sequence coding for the tetracycline silencer (tTS) under the control of the left ITR. Transcription of the tTS gene ends at the left SV40 bidirectional transcription termination signal which also serves for termination of transcription of the EGFP gene.

Plasmide

PTR-tetON-tTA-hGDNF is derived from PTR-tetON-tTA-EGFP. EGFP was replaced by the hGDNF cDNA (gene bank accession n° L19062: nt1-151 and L19063: nt1-485.

Transfection

Figure 4:
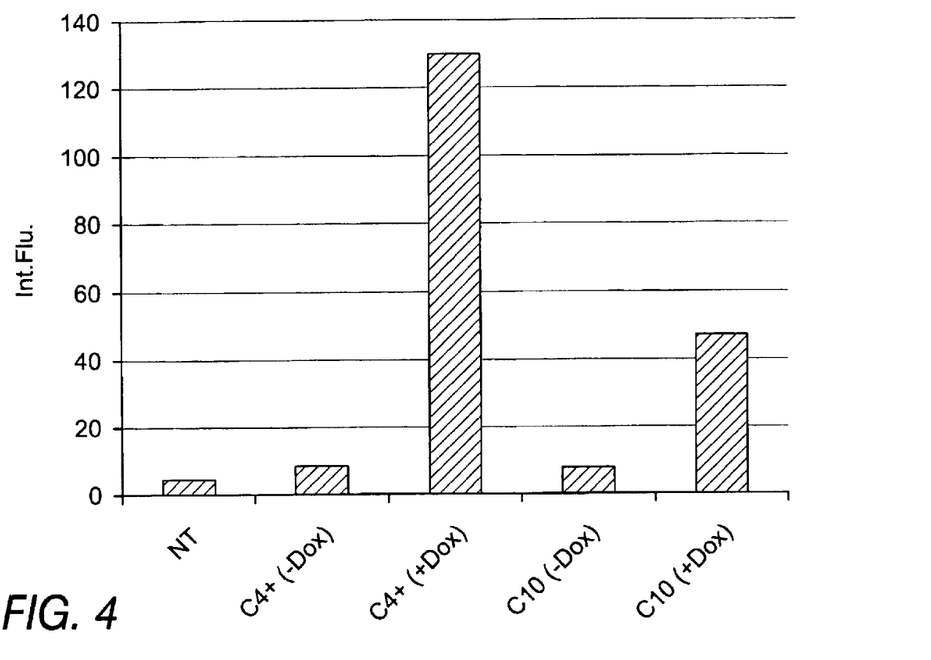
FIG. 4 shows the results of a transient transfection analysis on 293T cells transfected with pTR-tetON-tTA-hGDNF plasmidic clones with the C4 or C10 promoter.

PTR-tetON-tTA-EGFP was transfected into 293T cells using the calcium-phosphate co-precipitation method. DMEM culture medium containing doxycycline (1 µg/ml) or not was added to the cells. Forty-eight hours after transfection, i) the cells were harvested and FACS analyzed or ii) the cells were lysed and protein extracts were prepared for fluorimetric measure of gfp protein content. FIG. 4 shows the data obtained for 2 different pTR-tetON-tTA-hGDNF plasmidic clones after transient transfection into 293T cells. The fluorescence intensity was respectively 29.8 fold (C4) and 12.3 fold (C10) higher in the presence than in the absence of doxycycline.

Figure 5:
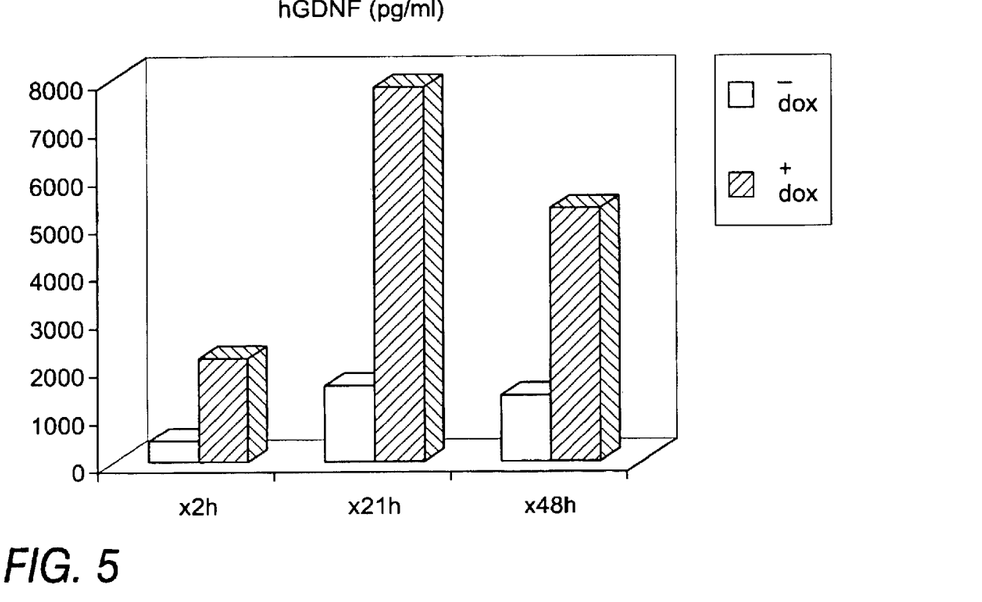
FIG. 5 shows the concentrations of hGDNF in transfected 293T cells in the presence or absence of doxycycline after 2 hrs, 21 hrs and 48 hrs of exposure in fresh culture medium.

PTR-tetON-tTA-hGDNF was transfected into 293T cells using the calcium-phosphate co-precipitation method. Forty-eight hours after transfection, the culture medium was replaced by fresh medium and the conditioned medium harvested 2 hrs, 21 hrs or 48 hrs after and analyzed by ELISA (see FIG. 5). FIG. 5 shows the concentration of GDNF released by the transfected cells in the presence or in the absence of doxycycline. The hGDNF concentration was respectively 5-fold (2 hrs), 5-fold (21 hrs) and 4-fold (48 hrs) higher in the presence than in the absence of doxycycline.

REFERENCES

Bohl et al., 1998 Blood 92 (5): 1512–1517
Du B, et al. (1996) Gene Ther 3(3):254–61
During M J, et al. (1998) Gene Ther 5(6):820–7
Fan D, et al. (1998) Neuroeci Lett 22;248(1):61–4
Freese A, et al. (1997) Epilepeia 1997 Jul;38(7):759–66
Heberman RP et al., (1998) Gene Ther. 5: 1604–1611
KAPPLITT, M. G. et al. Nature Genet. 8 (1994) 148–154.
Kirik et al., 2000 J Neurosci. 20(12):4686–700
Klein et al., 1998 Exp Neurol. 150(2);183–94
Lo, W. D. et al. Hum. Gene Ther. 20 (1999) 201–213.
McCown T J et al., 1996 Brain Rea. 713:99–107
McLaughlin et al., 1988 J. Virol. 62(6):1963–73
Samuleki et al., 1982 Proc Natl Acad SciU S A. 79(6): 2077–81
Samulaki et al., 1989 J. Virol. 63:3822–3828
L. Tenenbaum , M. et al. Gene Ther. 6 (1999) 1045–1053.
Wu P, et al. J Virol 72(7):5919–26
Zolotukhin et al., 1999 Gene Ther. 6(6);973–85

What is claimed is:

1. An adeno-associated virus vector comprising:
   an antibiotic inducible/repressible genetic construct for controlling the transciption of a gene of interest by a cell, wherein said genetic construct comprises a bi-directional antibiotic controlled activator-responsive promoter/operator sequence, said bi-directional antibiotic controlled activator-responsive promoter/operator sequence being located between a gene of interest and a cistron, wherein said bi-directional antibiotic controlled activator-responsive promoter/operator sequence controls the transcription of said gene of interest and of a cistron, and wherein said cistron encodes an antibiotic-controlled transactivator; and two bi-directional polyadenylation sequences (poly-A), wherein one of said bi-directional polyadenylation sequences is located between said gene of interest and a viral terminal sequence and the other bi-directional polyadenylation sequence is located between said cistron and a viral terminal sequence, wherein the antibiotic is tetracycline or an analog of tetracycline.

2. The vector according to claim 1, wherein the bi-directional promoter/operator sequence comprises a tetracycline responsive element (TRE) comprising 7 copies of a 42 base pair sequence of the tetracycline operator sequence, wherein said TRE is located between two mini CMB-promoters.

3. The vector acording to claim 1, further comprising a second cistron downstream of the first cistron encoding the antibiotic-controlled transactivator, wheren said second cistron comprises at least one gene or interest and an internal ribosome entry site (IRE) positioned between said gene of interest and said first cistron.

4. The vector according to claim 1, wherein said viral terminal sequences comprise encapsidation, integration and replication genetic sequences from adeno-associated viruses.

5. The vector according to claim 1, further comprising a sequence encoding an antibiotic silencer sequence, located between said two viral terminal sequences and said two bi-directional polyadenylation sequences.

6. The vector according to claim 1, wherein the gene of interest in the genetic construct is a therapeutic gene.

7. The vector according to claim 6 wherein the therapeutic gene is selected from the group consisting of: anti-apoptotic genes, neurotrophic factors, enzymes involving the detoxification of free radicals, tumor specific antigens, fusogenic enzymes involving the detoxification of free radicals, tumor specific antigens, fusogenc peptides, erythropoetin (EPO), human growth factor, tissue plasminogen activator (TPA), granulocyte macrophage colony stimulator factor (GMCSF), coagulation factors, insulin, calcitonyn, thymidine kynase, interleukins, interferons and tumor necrosis factor.

8. The vector of claim 7 wherein said neurotrophic factors are selected from the group consisting of: GDNF, BDNF, NT4 and CNTF.

9. An islolated cell or tissue transfomed by the vector of claim 1.

10. A method for improving the survival of a graft obtained fom fetal-nervous tissues comprising:
   obtaining cells for said graft from fetal-nervous tissues;
   transfecting said cells for said graft with an AAV-vector according to claim 1 wherein said AAV-vector comprises a genetic sequence encoding a neurotrophic factor and wherein the transfection with said AAV-vector induces a genetic modification of said cells; and
   transplanting said transfected cells into a host thereby creating said fetal-nervous tissue graft,
whereby the expression of the neurotrophic factor extends the survival period of said fetal-nervous tissue graft compared to untransfected cells.

11. An isolated cell from fetal-nervous tissue which has been transfected with an AAV-vector according to claim 1, wherein said vector comprises a genetic construct encoding a neurotrophic factor.

12. The isolated cell of claim 11, wherein said fetal-nervous tissue is a mesencephalic or striatal fetal-nervous issue.

13. The vector of claim 1, wherein the two bidirectional polyadenylation sequences (poly-A) are SV40 poly-A sequences.

* * * * *

SEQUENCE LISTING

<160> NUMBER OF SEQ ID NOS: 2

<210> SEQ ID NO 1
<211> LENGTH: 36
<212> TYPE: DNA
<213> ORGANISM: Artificial Sequence
<220> FEATURE:
<223> OTHER INFORMATION: PCR primer

<400> SEQUENCE: 1
atgaagcttg gtctacggag accggatccg aggtgc                    36

<210> SEQ ID NO 2
<211> LENGTH: 34
<212> TYPE: DNA
<213> ORGANISM: Artificial Sequence
<220> FEATURE:
<223> OTHER INFORMATION: PCR primer

<400> SEQUENCE: 2
ggtctagatc tctggagcca gggtcagata catc                      34